United States Patent [19]

Akino et al.

[11] Patent Number: 5,156,950
[45] Date of Patent: Oct. 20, 1992

[54] QUANTITATION OF HUMAN PULMONARY SURFACTANT AND REAGENT KIT TO BE USED THEREFOR

[75] Inventors: Toyoaki Akino; Yoshio Kuroki, both of Hokkaido; Kenji Hosoda, Saitama; Hideaki Suzuki, Tokyo, all of Japan

[73] Assignee: Teijin Limited, Osaka, Japan

[21] Appl. No.: 638,026

[22] Filed: Jan. 7, 1991

Related U.S. Application Data

[63] Continuation of Ser. No. 9,969, Feb. 2, 1987, abandoned.

[30] Foreign Application Priority Data

May 31, 1985 [JP] Japan .................................. 60-116738
Mar. 12, 1986 [JP] Japan .................................. 61-52563

[51] Int. Cl.$^5$ .................... G01N 33/53; G01N 33/577
[52] U.S. Cl. ........................ 435/7.51; 435/7.9; 435/7.94; 435/962; 435/975; 436/518; 436/548
[58] Field of Search ............ 436/548, 518, 808; 435/7.5, 7.9, 7.94, 975; 530/387, 389

[56] References Cited

U.S. PATENT DOCUMENTS

| | | | |
|---|---|---|---|
| 4,474,892 | 10/1984 | Murad et al. | 436/548 |
| 4,535,057 | 8/1985 | Dreesman et al. | 436/548 |
| 4,562,003 | 12/1985 | Lewicki . | |
| 4,656,253 | 4/1987 | Lewicki | 436/808 |

OTHER PUBLICATIONS

Kohler et al., Nature, vol. 256, pp. 495-497 (Aug. 7, 1975).
Phelps et al, Biochim. Biophys. Acta, vol. 791, pp. 226-238 (1984).
Chemical Abstracts, vol. 102, No. 3, Jan. 21, 1985, p. 517, Abstract No. 22517a.
Chemical Abstract, vol. 99, No. 7, Aug. 15, 1983, pp. 324-325, Abstract No. 509z.
*Chemical Abstracts*, 106:153652w (1987).

*Primary Examiner*—Esther L. Kepplinger
*Assistant Examiner*—Carol E. Bidwell
*Attorney, Agent, or Firm*—Sughrue, Mion, Zinn, Macpeak & Seas

[57] ABSTRACT

A method of quantitation of human pulmonary surfactant characterized by determining the quantity of human pulmonary surfactant in the test sample according to the immunological method by use of the primary monoclonal antibodies which recognize the human pulmonary surfactant apoproteins and the labeled secondary monoclonal antibodies which recognize said apoproteins but bind to a part of the antigen which is different from the one to which the primary monoclonal antibodies bind, and a reagent kit to be used for the quantitation.

9 Claims, 4 Drawing Sheets

—○— Test substance, 0.25M $Mg^{++}$

—△— Test substance, $Mg^{++}(-)$

—●— Test substance, 0.25M $Mg^{++}$

—▲— Test substance, $Mg^{++}(-)$

QUANTITATION OF HUMAN PULMONARY SURFACTANT AND REAGENT KIT TO BE USED THEREFOR

This is a Continuation of application Ser. No. 07/009,969 filed Feb. 2, 1987 now abandoned.

TECHNICAL FIELD

The present invention relates to the quantitation of the human pulmonary surfactant conducted with the use of monoclonal antibodies against the human pulmonary surfactant apoproteins and a reagent kit to be used for such purposes.

BACKGROUND OF THE ART

The alveoli of the lung of the animal are lined with a physiologically active substance which mainly comprises phospholipid and is called a pulmonary surfactant. While covering the inner walls of alveoli, this substance acts to protect the alveolar epithelium and has an important physiological function for the animal to maintain its respiratory function. More particularly, it is said that the pulmonary surfactant exerts a specific surface action to cause changes in the surface tension of the inner surfaces of alveoli in response to expiration and inspiration, thus contributing to the maintenance of stability among the alveoli and displaying the antiatelectasis activity as well. The insufficiency of such a pulmonary surfactant invites the collapse of the alveoli making them impossible to keep the stabilized ventilation and thus causing the idiopathic respiratory distress syndrome (IRDS) which is sometimes seen with newborns.

Means can be adapted to prevent a newborn from being born with such a syndrome: when the result of the determination of the pulmonary surfactant content in the amniotic fluid, which is correlated to the growth of the fetal lungs, shows that the fetus is going to be born with immature lungs, it is possible to exercise such intrauterine therapy for the fetus as augmentation of secretion of the pulmonary surfactant by the administration of steroids.

As regards the methods of determining or estimating the content of pulmonary surfactant in the amniotic fluid, several methods have hitherto been proposed. For instance, there is a method in which the L/C ratio (ratio between lecithine and sphingomyelin) in the amniotic fluid is determined and another method in which the amount of dipalmitoyl phosphatidyl choline (DPPC) in the amniotic fluid is measured at the marker of the pulmonary surfactant; however, the former has a demerit of presenting a low correlation with IRDS since the method does not determine the phospholipid content which is the main component of the pulmonary surfactant and the latter involves a problem of having a low sensitivity. Incidentally, about 90% of the pulmonary surfactant is lipids such as phospholipid and neutral lipid and about 10% is protein. They exist as a complex of lipid and protein, i.e. as a lipoprotein. The removal of lipids from the pulmonary surfactant gives water insoluble protein, which is called apoprotein mainly composed of protein with molecular weight of about 36,000 (36K). Since protein excels phopholipid in specificity and can be detected at higher sensitivity, studies have been made to use the protein as the marker of the pulmonary surfactant and immunological quantitation by use of polyclonal antibodies has also been attempted. However, problems are also found with the method, in which polyclonal antibodies are used, in that the determination procedure takes a long time and that the sensitivity is not enough.

For carrying out the determination of a very small amount of the pulmonary surfactant contained in such a test substance as amniotic fluid in a short time with high sensitivity, it is necessary to obtain monoclonal antibodies that react against the pulmonary surfactant, thus solving all the abovementioned problems, but such monoclonal antibodies have not been obtained yet up to now.

DISCLOSURE OF THE INVENTION

The present inventors have conducted investigations into the immunoassay with the use of two kinds of monoclonal antibodies which are specific to the apoprotein obtained by separating and refining the pulmonary surfactant apoproteins from the lung and bronchus lavage fluids of patients with alveolar proteinosis which induces the rich accumulation of pulmonary surfactant. The result is the finding that the two kinds of monoclonal antibodies proposed by the present invention are very useful as the reagent to be used for the quantitation of the pulmonary surfactant, thus achieving the present invention.

To be more particular, the present invention relates to a method of quantitation of human pulmonary surfactant characterized by determining the quantity of human pulmonary surfactant in the test substance according to the immunological method by use of the primary monoclonal antibodies which recognize the human pulmonary surfactant apoproteins and the secondary monoclonal antibodies which recognize said apoproteins but bind to a part of the antigen which is different from the one to which the primary monoclonal antibodies bind.

BEST MODE OF CARRYING OUT THE INVENTION

Of the monoclonal antibodies of this invention, the especially desirable ones from the viewpoint of reactivity and stability are those antibodies which recognize apoproteins with molecular weights of about 62,000 and/or about 34,000 to 37,000, and are mouse antibodies of the IgG type.

The monoclonal antibodies of this invention can be obtained by fusing antibody-producing cells of animals immunized preferably with the human pulmonary surfactant apoproteins and myeloma cells to give hybridomas productive of monoclonal antibodies which recognize said apoproteins; culturing said hybridomas and/or cell lines arising therefrom; and collecting monoclonal antibodies, which recognize the human pulmonary surfactant apoproteins, from the culture.

In this invention, the pulmonary surfactant is isolated and collected from human lung and/or branchus lavage fluid, preferably from bronchus and lung lavage fluid of patients with alveolar proteinosis. The pulmonary surfactant is a complex (lipoprotein) composed of about 90% lipids and about 10% protein. The pulmonary surfactant is obtained by the method described by Frosolono (see J. Lipid Res. 11, 439~457 (1970)) and the removal of lipids therefrom gives the apoprotein proposed in this invention. Apoprotein is mainly composed of proteins with a molecular weight of about 62,000 and about 36,000 respectively. Proteins with a molecular weight of 36,000 are separated as a wide band when subjected to sodium dodecyl sulfate-polyacrylamide gel electrophoresis (SDS-PAGE) and it is deemed that proteins with a molecular weight of about 34,000 are contained therein. The apoproteins of this invention accordingly include these proteins and all other apoproteins and their fragments. The molecular weights of the proteins were determined with SDS-PAGE.

Hybridomas productive of monoclonal antibodies which recognize the apoproteins can be produced according to the cell fusion method whose procedures are generally known per se. Firstly, such animals as monkeys, horses, bovines, goats, sheep, rabbits, rats, mice, etc. are immunized with apoproteins, then antibody-producing cells (lymphocytes) are collected from the spleens and lymph nodes of these immunized animals, followed by cell fusion of these cells with human or animal myeloma cells. As the myeloma cells, mouse myeloma cells may be used most conveniently. The examples of such mouse myeloma cells include P3-X63-Ag8, P-X63-Ag8-U1, P3-NS1/1-Ag4-1, P3-X63-Ag8 6.5.3, SP2/0-Ag14, FO, and MPC 11-45.6TG1.7.

The conditions of cell fusion are as follows. For instance, antibody-producing cells and myeloma cells are mixed at a ratio of 10:1 to 1:10, preferably at a ratio of 1:1 to 1:3. An appropriate cell fusion mixture such as RPMI 1640 containing about 35% polyethylene glycol (molecular weight approximately 1,000 to 6,000) and about 7.5% dimethyl sulfoxide is added to the cell mixture and are stirred for one to several minutes at room temperature to 37° C. Thereafter the mixture is diluted little by little with RPMI 1640 containing 10% FCS (fetal calf serum), washed, and ajusted to have a cell concentration of 1 to $5 \times 10^5$ cells/ml with a selective liquid culture medium HAT (hypoxanthine-aminopterin-thymidine). The thus prepared culture liquid is added to a 96-well plate, for instance, in portions of 0.2 ml per well, and cultured in 5% $CO_2$ air at 35°~38° C. for 2 to 3 weeks. In the HAT liquid culture medium, only hybridomas can survive and 8-azaguanine resistant myeloma cells and fused cells between myeloma cells cannot survive (unfused antibody-producing cells perish in the course of several days). Then from the colonies of hybridomas, only those hybridomas that secrete monoclonal antibodies reactive against apoproteins are selected. This process of selection (or screening) can be carried out by subjecting the monoclonal antibodies produced by the respective hybridomas to the enzyme-linked-immunosorbent assay to examine if they undergo the antigen-antibody reaction with the desired apoproteins. The hybridomas, which secrete monoclonal antibodies this invention aims at, must then be subjected to cloning to obtain clonal cells. This cloning can be effected, for instance, by limiting dilution to monoclonality. About 2 to 3 weeks later, the colonies grown in a 96-well plate are collected to have their antibody activity against apoproteins examined again by the enzyme-linked-immunosorbent assay and the selected hybridomas are cultured to give monoclonal antibodies specific to the apoproteins.

Another method of obtaining monoclonal antibodies is to infect the antibody-producing cells with Epstein-barr virus (hereinafter abbreviated as E-B virus) to prepare transformed cells. The transformed cells and/or cell line arising therefrom are cultured and monoclonal antibodies which bind to apoproteins are collected from the culture.

E-B virus is a virus, which belongs to the herpes virus, regarded to be a virus causative of Burkitt's lymphoma and rhinopharynx cancer. The antibody-producing cells are infected with E-B virus and cultured for about 2 to 3 weeks in a 5% $CO_2$ incubator to establish transformed cells forming many heterogeneous colonies. Then selections are made from these transformed cells according to the same method as mentioned above to obtain only those which secrete monoclonal antibodies specific to apoproteins and then cloning follows to obtain cloned transformed cells according to the cloning method described above.

Then in this invention, the selected hybridomas or transformed cells are cultured to establish desired specific monoclonal antibodies. The hybridomas or transformed cells, selected by cloning and productive of antibodies which recognize the pulmonary surfactant apoproteins, can be freezestored and also can be mass-cultured according to a proper method. And monoclonal antibodies, which bind specifically to apoproteins, can be obtained from the culture supernatants. When these cells are transplanted to animals to develop tumors, the desired antibodies can be obtained from their ascites and serum. The purification of the monoclonal antibodies of this invention can be carried out by affinity chromatography by use of protein A.

In this invention, two kinds of monoclonal antibodies, PC6 and PE10, which recognize human pulmonary surfactant apoproteins, were obtained. They were monoclonal antibodies which recognize different epitopes in the apoprotein antigen.

It has therefore been made possible to conduct a two-antibody sandwich enzyme-linked immunosorbent assay (ELISA).

Quantitation of apoproteins was carried out with the highest sensitivity in ELISA with the combined use of solid-phase PC6 and biotinylated PE10. Sandwich ELISA of this type was performed to determine the pulmonary apoproteins of various kinds of animals and humans, thus producing the results that the assay could determine the human lung lavage and human amniotic fluid only and could not determine other animals' lung lavage and human serum at all. It was made apparent from the above that the two types of antibodies were specific to human lung and amniotic fluid and that the apoproteins in this invention were not arising from the serum.

The time required for determination was shortened according to this two-site simultanous immunoassay, in which the first monoclonal antibodies (primary antibodies) fixed to a microplate, antigens (apoproteins), and biotinylated second monoclonal antibodies (secondary antibodies) were made to react with each other simultaneously. Also, the use of skim milk in the blocking agent lowered the background values remarkably.

It is advisable in this invention to have the primary antibody fixed to a carrier and the method of fixation may be chosen from the publicly known ones. As the carrier, those which are solid-phase ones including balls, beads, gears, and microplates made of polystyrene, polyethylene, polyacrylate, Teflon, or polyacetal may be used preferably.

No limit is placed upon the method and procedure of labeling and the method may employ any procedure of detection. Any known methods and procedures such as determination by the secondary reaction with anti-immunoglobulin antibody or Staphylococcus protein A may be adopted. As the labeling agents, such enzymes as horseradish peroxidase, $\beta$-D-galactosidase, and alkaline phosphatase are used in the enzyme immunoassay (EIA), $^{125}$I and $^3$H in the radioimmunoassay (RIA), and fluorescein-isothiocyanate in the fluorescence immunoassay (FIA) in general; however, other labeling agents may also be used so far as their activity is assayable.

In the case where the labeling agent is an enzyme, a substrate is used for assaying its activity. As the substrate, 2,2'-azinodi-[3-ethylbenzthiazoline sulfonic acid-]ammonium acid (ABTS)-$H_2O_2$, 5-amino salicylic acid-$H_2O_2$, O-phenylenediamine-$H_2O_2$, and 4-aminoantipyrine-$H_2O_2$ may be used as the substrate for horseradish peroxidase, and fluoresein-di-($\beta$-D-galactopyranoside) and O-nitrophenol-$\beta$-D-galactopyranoside for $\beta$-D-galactosidase. In performing the assay, such publicly known reagents as solubilizer, detergent, and reaction terminator are used besides the above-mentioned reagents.

What is desirably used in this invention is a combination of a biotinylated antibody and an enzyme-labeled avidin. Avidin is a basic glycoprotein with a molecular weight of about 68,000 existing in the albumen and is understood to have a very high affinity (affinity constant $10M^{-1}$) for biotin which is known as vitamin H. It is known that avidin is composed of 4 subunits and what is called avidin in the present invention includes these subunits.

This invention also includes the aforementioned antibodies and a kit of reagents in its scope. A desirable example includes: (1) the first monoclonal antibody (primary antibody) fixed to a carrier recognizes a human pulmonary surfactant apoprotein; (2) labeled second monoclonal antibody (secondary antibody) which recognizes said apoprotein but binds to a part of the antigen which is different from the one to which the primary monoclonal antibody binds; and (3) reagents, which mainly comprise reagents for detecting said labeled antibody, to be used for determining the plumonary surfactant existing in the human amniotic fluid and human lung or bronchus lavage fluid, if necessary.

In performing the quantitation according to the present invention, it is desirable to conduct the immunoreaction at a temperature ranging from 40° C. to 50° C. exclusive. It is also desirable to have magnesium ions ($Mg^{++}$) present in the immunoreaction system. In this invention, difference in reactivity between a standard made of apoprotein and the pulmonary surfactant in the test substance such as amniotic fluid is observed in the immunoassay. It may be a safe assumption that such difference is attributable to the steric hindrance caused by the fact that the pulmonary surfactant in the test substance is composed of apoproteins and phospholipid which is present in an amount ten times as much as the apoproteins.

The present inventors have found that the apoproteins and the lipoproteins contained in the pulmonary surfactant of the test substance come to display the same behavior in a short time upon immunological observation by adjusting the temperature and having $Mg^{++}$ present in the assay, thus making it possible to achieve the solid-phase enzyme immunoreaction in a short time.

The following Examples illustrate the present invention:

EXAMPLE 1

(1) The lungs and bronchi of patients with alveolar proteinosis were laved with 0.15M sodium chloride aqueous solution for therapeutic purpose and 3 l of bronchoalveolar lavage fluid (BALF) were collected. This BALF was centrifuged at 300×g for 10 minutes and the cells and cell debris were removed. Then the obtained supernatant was centrifuged at 48,000×g for 20 minutes to collect the sedimented fraction.

This sedimented fraction was suspended in 80 ml of 10 mM Tris buffer (pH 7.4) containing 145 mM sodium chloride and 1 mM disodium ethylenediaminetetraacetic acid. The suspension was layered on a discontinuous gradient prepared with 0.25M and 0.65M sucrose solutions and centrifuged at 40,000×g for 60 minutes.

The interface fraction (IB fraction) containing the pulmonary surfactant separated between 0.25M and 0.65M sucrose solutions was collected and resuspended in 400 ml of the same buffer. This suspension was centrifuged at 48,000×g for 30 minutes to obtain the sediment (pulmonary surfactant).

To remove the impurities such as albumin from the sediment, the sediment was dispersed gently in 27 ml of 5 mM Tris buffer (pH 7.8) containing 1% Triton X-100 (polyoxyethylenealkylphenyl ether), 3 mM EDTA, 1 mM phenylmethylsulfonyl fluoride, and 0.5 mM dithiothreitol (hereinafter referred to as Triton buffer). This dispersion was centrifuged at 150,000×g for 60 minutes to obtain a precipitate (purified pulmonary surfactant).

This precipitate was redispersed in 4 ml of the above-mentioned Triton buffer and 4 ml of a butanol-methanol mixture (6:1 v/v) was added thereto. The mixture was shaken vigorously and left standing at 0° C. for 10 minutes. After the removal of lipid by extraction, the dispersion was centrifuged at 2,000 r.p.m. for 15 minutes to obtain a precipitate (apoprotein). This procedure was repeated three times to give a final precipitate of apoprotein (LS apoprotein).

This precipitate was dispersed in 20 ml of Triton buffer and dialyzed against the same Triton buffer with the use of a cellophane membrane (to have butanol-ethanol solution removed) to obtain in a dialysate. This dialysate was centrifuged at 15,000×g for 60 minutes to obtain a supernatant. The sediment was solubilized by addition of 20 ml of Triton buffer and centrifuged at 150,000×g for 60 minutes to give a supernatant. This procedure was repeated six times to collect supernatants. The thus obtained supernatants were pooled to give a total of 150 ml. The pooled supernatant was applied onto a Blue Sepharose 4B column (1.8 cm diameter×3.5 cm) and eluted by use of the same buffer and the void fractions were collected to remove albumin thoroughly.

The collected void fractions were applied onto a DEAE-Toyopearl column (diameter 1.4 cm×19 cm)

equilibrated with the Triton buffer, eluted with 200 ml of the same buffer at a flow rate of 15 ml/hr at first, then the elution was continued while linearly increasing the concentration of sodium chloride in the same buffer from 0 to 0.5M continuously and fractions eluted while the sodium chloride concentration was in the range of 0.30M and 0.35M were collected. The proteins contained in these fractions proved to have a molecular weight of about 62,000 and about 36,000 respectively.

(2) LS apoproteins contained in the aforementioned fractions eluted while the sodium chloride concentration was between 0.30M and 0.35M were used in the experiment described below.

The LS apoproteins were emulsified in Freund's complete adjuvant and injected into the peritoneal cavities of BALB/C mice. The mice were boosted with the same LS apoproteins 30 days later. On the other hand, myeloma cell line P3-X63-Ag8-U1 had been maintained for incubation in RPMI 1640 (Gibco) supplemented with 15% fetal calf serum. Three days after the boosting, the spleen cells obtained from the mice were fused with P3-X63-Ag8-U1 by use of polyethylene glycol 4000 according to the method proposed by Oi et al. (see Selective Methods in Cellular Immunology 1980, pp. 351~372) and distributed onto the 96-well microplates. After the cell fusion, the medium was replaced with RPMI medium supplemented with 100 μM hypoxanthine, 0.4 μM aminopterin, and 16 μM thymidine (HAT medium). During the culture in the HAT medium for a period of 2 to 3 weeks, only the hybridomas of spleen cells and myeloma cells were found growing. The antibody activity of the hybridoma culture medium was examined by ELISA described below.

Screening of the Antibodies

The LS apoproteins were attached to ELISA plates and were subjected to the blocking by use of 3% (W/V) BSA (bovine serum albumin) in 10 mM phosphate-buffered saline (pH 7.4). After blocking, 50 μl of the hybridoma culture medium was added to the abovementioned plates and incubated at room temperature for 2 hours or at 4° C. overnight. Thereafter, a secondary antibody of 50 μl horse biotinylated anti-mouse IgG immunoglobulin (2 μg/ml) was added and incubated at room temperature for 1 hour. 50 μl of horseradish peroxidase avidin D solution (1 μg/ml) was added thereto and antibodies bound to the LS apoproteins were detected by adding 100 μl of substrate solution (0.1% o-phenylelediamine, 0.015% $H_2O_2$, 0.1M citrate buffer, pH 4.6).

(3) Hybridomas productive of antibodies against LS apoproteins were selected and cloned in limiting dilution to monoclonality, finally giving two kinds of monoclonal hybridomas. These two kinds of hybridomas were respectively amplified in pristane-treated BALB/C mice abdominal cavities to obtain ascites containing the monoclonal antibodies. Thus obtained ascites were made to have their antibodies precipitated with the use of 50% saturated ammonium sulfate, and the precipitate was dissolved in 0.1M phosphate-buffered saline (pH 8.0). After having been dialyzed, the solution was placed on a Protein A-Sepharose CL 4B column (Parmacia Fine Chemicals) and the antibodies were eluted with 0.2M glycine-hydrochloride buffer (pH 3.0) to be purified.

The monoclonal antibodies obtained from the two kinds of hybridomas were named PC 6 and PE 10 respectively.

(4) Properties of the monoclonal antibodies.

In the Western blotting method, PC 6 and PE 10 recognized two types of apoproteins 36 K and 62 K obtained from the IB fraction of bronchoalveolar lavage fluids of patients with alveolar proteinosis. The same two antibodies also recognized the apoproteins 37 K, 34 K, and 62 K in the human amniotic fluid and normal human bronchoalveolar lavage fluids. The 36 K proteins were separated with SDS-PAGE as a wide band and as 37 K and 34 K proteins are contained among them, the 35 K proteins are the same proteins as the 37 K and 34 K proteins. It was found that PC 6 and PE 10 recognized the epitopes (antigen determinants) neighboring and yet differing from each other from the result of the cross reaction conducted by the dot-immunobinding method. These antibodies were specific to human pulmonary surfactant apoproteins and did not react with pulmonary surfactant apoproteins of animals such as rats, swine, rabbits and human serum proteins.

Western blotting technique

The antigens specific for monoclonal antibodies were identified using the western blotting technique by the method of Towbin et al. (Pro. N. A. S., vol. 76, pp. 4350~4354).

First, the antigens containing pulmonary surfactant apoproteins were subjected to SDS-PAGE. The proteins were then transferred from the slab gel to a nitrocellulose sheet after SDS-PAGE with the electrode buffer (pH 8.3) containing 25 mM Tris-hydrochloride, 192 mM glycine, and 20% (v/v) methanol and a voltage gradient of 7 V/cm applied for 2 hours. Each lane of the nitrocellulose sheet was cut off. One lane was used for staining the proteins by Amido black, and the others were subjected to an enzyme immunoassay mentioned below.

After blocking the sheet with 3% (W/V) BSA/PBS (0.01M phosphate buffer containing 0.85% NaCl), monoclonal antibody (PC 6 or PE 10) was added as primary antibody. Thereafter, horse biotinylated anti-mouse IgG immunoglobulin was added as secondary antibody. Each sheet was washed in PBS containing 0.05% (V/V) Tween-20. After the incubation with horseradish peroxidase avidin D, a substrate solution (0.05% diaminobenzidine, 0.03% $H_2O_2$, 0.01 MPBS) was added to detect and identify the antigen protein.

EXAMPLE 2

(1) Preparation of insolubilized monoclonal antibody (Fixing of monoclonal antibody to a carrier)

Wells of the non-treated microtiter plates (Dynatech Laboratories, Inc.) were filled with 200 ml of 0.1M sodium hydrogencarbonate aqueous solution containing 10 μg/ml of monoclonal antibody PC 6 and incubated at 20° C. overnight. Then, the solutions in the respective wells were removed by suction and PBS (0.01M phosphate buffer containing 0.85% NaCl, pH 7.4) solution containing 2% skim milk and 1% Triton X-100 (hereinafter referred to as TX/SM/PBS solution) was added thereto to conduct the post-coating treatment at room temperature for 30 minutes. After the treatment was over, the microtiter plates were washed in the aforementioned solution and were stored at −20° C. until they were used.

(2) Preparation of biotin labeled monoclonal antibodies

After a PBS solution of monoclonal antibodies PE 10 (1.0 mg/ml) was dialyzed against 0.1M sodium hydrogencarbonate aqueous solution, 10 volumes of monoclonal antibodies were mixed with 1 volume of N-hydroxysuccinimidobiotin (Pierce Chemical Co.) solution (1.0 mg/ml) in dimethylsulfoxide. The mixture was incubated at room temperature for 4 hours and then dialyzed against 50 mM PBS solution, thus obtaining biotin labeled monoclonal antibodies.

(3) Quantitation of pulmonary surfactant apoproteins by two-site simultaneous immunoassay After the microtiter plates fixed with monoclonal antibody PC 6 were returned to room temperature and washed in TX/SM/PBS solution, a TX/SM/PBS solution containing purified pulmonary surfactant apoproteins ranging from 10 ng/ml to 640 ng/ml was added to each well in a portion of 100 μl as the standard substance solution. Apart from this procedures, various dilutions ranging from 2 to 256 times of human amniotic fluid in TX/SM/PBS solution were added to each well of other plates in a portion of 100 μl as the test substance solution. Then a TX/SM/PBS solution containing biotinylated monoclonal antibody PE 10 (2 μg/ml) was added a portion of 100 μl to each well already filled with the aforementioned standard substance solution or test substance solution. The wells were incubated at 37° C. for 90 minutes, had their solutions removed by suction, and washed with a TX/SM/PBS solution.

The each well was filled with horseradish peroxidase (HRP) labeled avidin D (Vector Laboratories, Inc.) diluted 1,200 times in a TX/SM/PBS solution in a portion of 200 μl, incubated at room temperature for 20 minutes, had its solution removed by suction, and washed with a PBS solution containing 1% Triton X-100.

Figure 1:
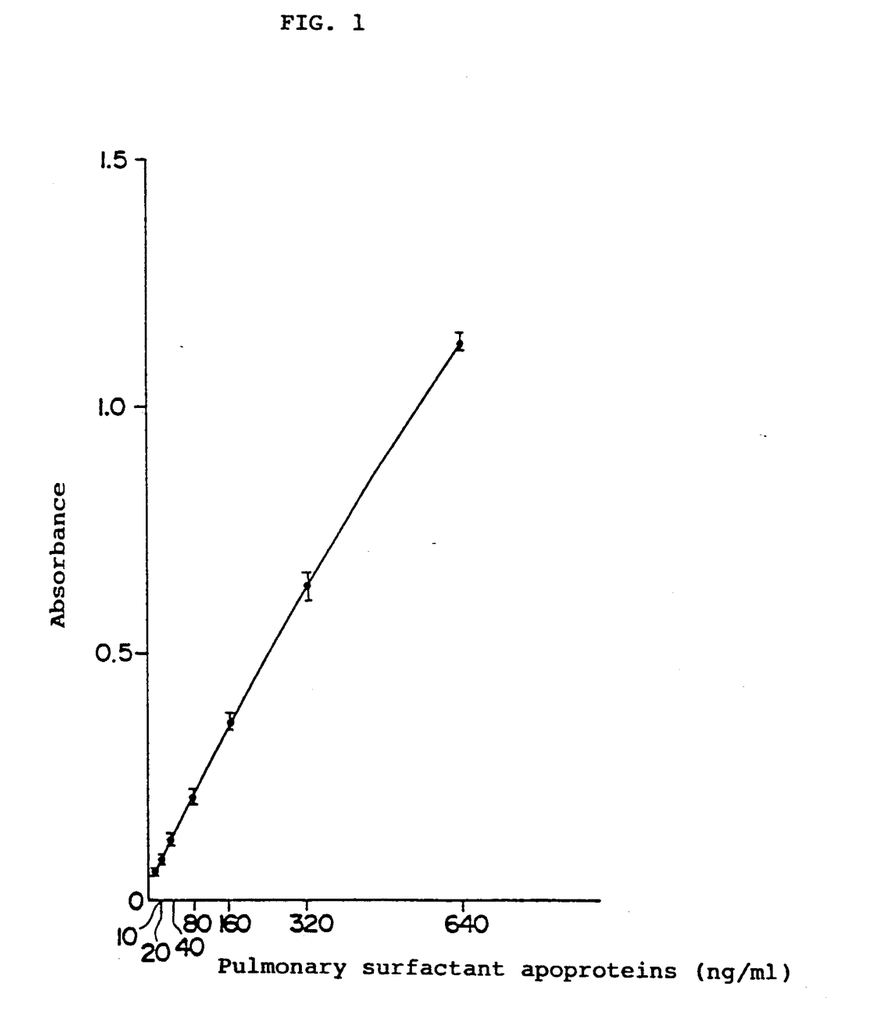
FIG. 1 shows a calibration curve for the two-site simultaneous immunoassay conducted using one of the monoclonal antibodies immobilized on a microtiter plate.

Thereafter, a substrate solution comprising 0.1M citrate buffer (pH 4.6) containing 0.1% o-phenylenediamine and 0.015% $H_2O_2$ was added to each well and the reaction was allowed to continue at room temperature for 30 minutes and then stopped by the addition of 100 μl of 2M sulfuric acid. After the reaction was stopped, the absorbance of each well was measured using an automatic microplate reader at two absorbance wave lengths; A500-A610. The absorbance change observed with different concentrations of the standard substance were plotted to prepare a calibration curve as shown in FIG. 1. Using this calibration curve, the concentrations of the respective test substances were obtained. According to this method, the concentrations of apoproteins in the 59 test substances of amniotic fluids from gestational 23 to 41-week women were determined and the result shown in Table 1 in which it was made clear that the concentrations of apoproteins increased as the gestational weeks increased. As seen from Table 1, the concentration of apoproteins was very low for the women of 30 weeks gestation or less. While the apoprotein concentration of the women of 34~36 weeks gestation was 6.5 times higher, and the concentrations for the women of 37 weeks gestation or more was as high as 15.5 times. The above fact indicates that the concentration of pulmonary surfactant apoproteins in the amniotic fluid increases remarkably as the time of childbirth approaches, and the aforementioned pattern of amniotic fluid apoprotein during the gestation period substantially agreed with the pattern taken by the increasing amniotic fluid phospholipid (L/C ratio, DPPC) throughout intrauterine life.

TABLE 1

| Duration of pregnancy (weeks) | Amniotic fluid apoprotein μg/ml | (case number) |
|---|---|---|
| ≦30 | 0.84 | (13) |
| 31~33 | 1.54 | (10) |
| 34~36 | 5.46 | (13) |
| 37~41 | 13.10 | (23) |

EXAMPLE 3

(1) Preparation of beads of insolubilized monoclonal antibodies

After polystyrene beads were thoroughly washed, they were placed in a PBS (pH 7.4) solution containing monoclonal antibody PC 6 at the concentration of 20 μg/ml and left at 4° C. overnight. Thereafter, the beads were washed in a PBS solution and then left standing in 0.5% BSA aqueous solution at 4° C. overnight for postcoating treatment to give beads of insolubilized monoclonal antibodies.

(2) Preparation of horseradish peroxidase-labeled monoclonal antibodies 50 ml of a dimethylformamide solution containing N-(m-maleimide benzoic acid)-N-succinimide ester (MBS) (10 mg/ml) was added to a PBS solution containing monoclonal antibody PE 10 (1.0 mg/ml) and the reaction was conducted at 25° C. for 30 minutes. The reaction mixture was then subjected to gel filtration with 0.1M phosphate buffer (pH 6.0) by use of a column filled with Sephadex G-25 to separate maleimidic monoclonal antibodies from unreacted MBS.

Besides the above procedure, an ethanol solution of N-succinimidyl-3-(2-pyridylthio) propionate (SPDP) (10 mg/ml) was added to a PBS solution containing horseradish peroxidase (HRP) (1.0 mg/ml) and the mixture was allowed to go through the reaction at 25° C. for 30 minutes. Then the reaction mixture was purified by gel filtration with 0.01M acetate buffer (pH 4.5) by use of a Sephadex G 25 column and the fractions containing pyridylsufided HRP were collected and concentrated approximately to about one-tenth of the original volume in a collodion bag on an ice bath. Then 1 ml of 0.1M acetate buffer (pH 4.5) containing 0.85% NaCl and 0.1M dithiothreitol was added thereto and the mixture was stirred at 25° C. for 30 minutes to reduce the pyridyldisulfide groups introduced into HRP molecules. The reaction mixture was then subjected to gel filtration by Sephadex G-25 column to obtain fractions containing thiolic HRP.

The maleimidic monoclonal antibodies and the thiolic HRP obtained in the above were mixed and concentrated to 4 mg of protein concentration in a collodion bag on an ice bath. The concentrate was left standing at 4° C. overnight and filtrated on a column of ultrogel Ac A44 to obtain HRP labeled monoclonal antibodies.

(3) Quantitation of apoproteins by two-site simultaneous immunosorbent assay (simultaneous sandwich ELISA)

A portion of the beads on which monoclonal antibody PC 6 was insolubilized, 200 μl of PBS solution (pH 7.4) containing purified pulmonary surfactant apoproteins ranging from 10 μg/ml to 640 μg/ml (standard substance) and 0.5% BSA and 1% Triton X-100, and 200 μl of PBS solution (pH 7.4) containing HRP-labeled monoclonal antibody PE 10 and 0.5% BSA and 1% Triton X-100 were placed in the respective test tubes and incubated at 37° C. for 1 hour. After the solution in each test tube was removed by suction, the tubes were washed with PBS containing 1% Triton X-100, and then 0.5 ml of 0.1M phosphate/citrate buffer (pH 4.5) containing 0.05% 2,2'-azinodi-3-ethylbenzthiazoline-6-sulfonic acid (ABTS) and 0.003% $H_2O_2$ was added to the respective test tubes. After incubation at 37° C. for 30 minutes, 1 ml of 0.2M oxalic acid aqueous solution was added to the respective test tubes as the reaction terminator to terminate the enzyme reaction.

Figure 2:
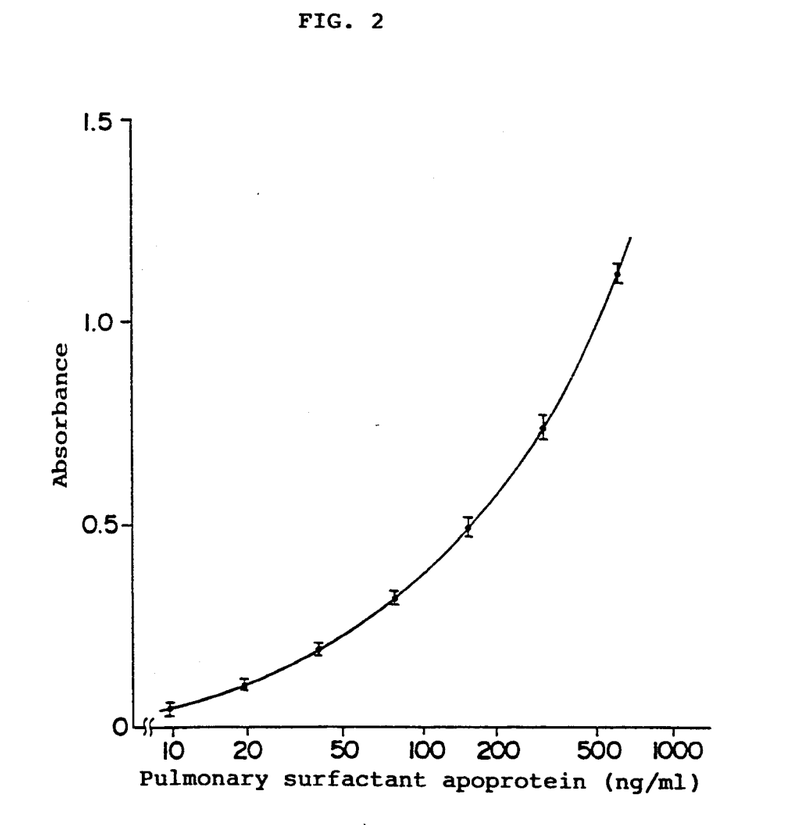
FIG. 2 shows a calibration curve for the two-site simultaneous immunoassay conducted using one of the monoclonal antibodies immobilized on a bead.

Then the absorbance of each solution was measured using a spectrophotometer at a wave length of 420 nm, the obtained absorbances were plotted against the concentration of the standard substance to obtain calibration curves of good concentration dependence. The result is shown in FIG. 2.

EXAMPLE 4

The quantitation of pulmonary surfactant apoproteins in the amniotic fluid at various temperatures was conducted with the use of a reagent kit obtained in Example 3.

A portion of the beads fixed with insolubilized monoclonal antibody PC 6; 200 μl of PBS solution (pH 7.4) which contains 1% BSA and purified pulmonary surfactant apoprotein at 10 mg/ml~300 mg/ml (standard substance) and 1% Triton X-100, or 200 ml of amniotic fluid diluted 10 times and 20 times (0.1% skim milk; 1% Triton X-100); and 200 μl of a solution containing HRP labeled monoclonal antibody PE 10 and 1% BSA and 1% Triton X-100 were added to respective test tubes and were incubated at various temperatures of 25° C., 37° C., 41° C., 45° C., 50° C., and 55° C. for 1 hour. After the solutions were removed from the test tubes by suction, the test tubes were washed with a saline solution. Then a mixture of 1% 3,3',5,5'-tetramethylbenzene-containing methanol solution/0.015 $H_2O_2$-containing 0.1M phosphate-citrate buffer (pH 4.4) mixed at a ratio of 3/7 (V/V) was added to the respective test tubes in a portion of 0.4 ml. After 15-mimute incubation at room temperature, 2 ml of 1.5$NH_2SO_4$ aqueous solution was added to the respective test tubes as the reaction terminator to have the enzyme reaction stopped.

Then the absorbance of each solution was measured using a spectrophotometer at a wave length of 450 nm. The result is shown in FIG. 3.

Figure 3:
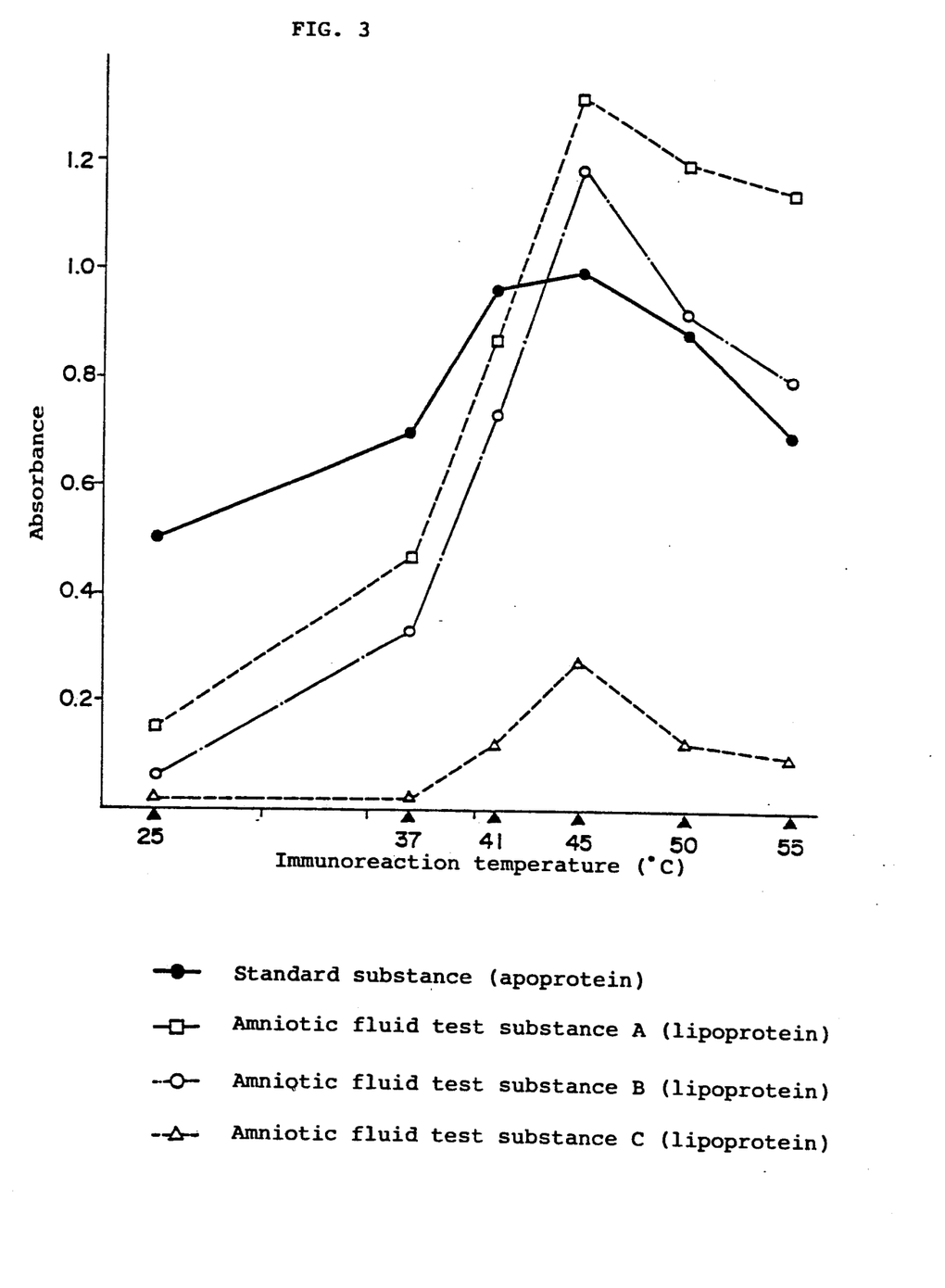
FIG. 3 shows the measured values (aspiration rate) of the pulmonary surfactant lipoprotein in the amniotic fluid versus temperature of the immunoreaction.

As is apparant from FIG. 3, it was found that the enzyme reaction proceeded most rapidly at 45° C. from the fact that the highest optical density reading was obtained at 45° C.

EXAMPLE 5

The test substances and HRP-labeled monoclonal antibody PE 10 were diluted respectively with buffers, (a) a TBS buffer containing 0.25M $MgCl_2$, 0.1% skim milk, and 1% Triton X-100 and (b) a TBS buffer containing 0.1% skim milk and 1% Triton X-100. The enzyme reactions were carried out respectively for a period of 30 minutes, 45 minutes, 1 hour, 1.5 hours, 2 hours, and 3 hours at 45° C. The concentrations of pulmonary surfactants in the amniotic fluid was read from the respective times of enzyme reaction by use of the calibration curve and were plotted in FIG. 4.

Figure 4:
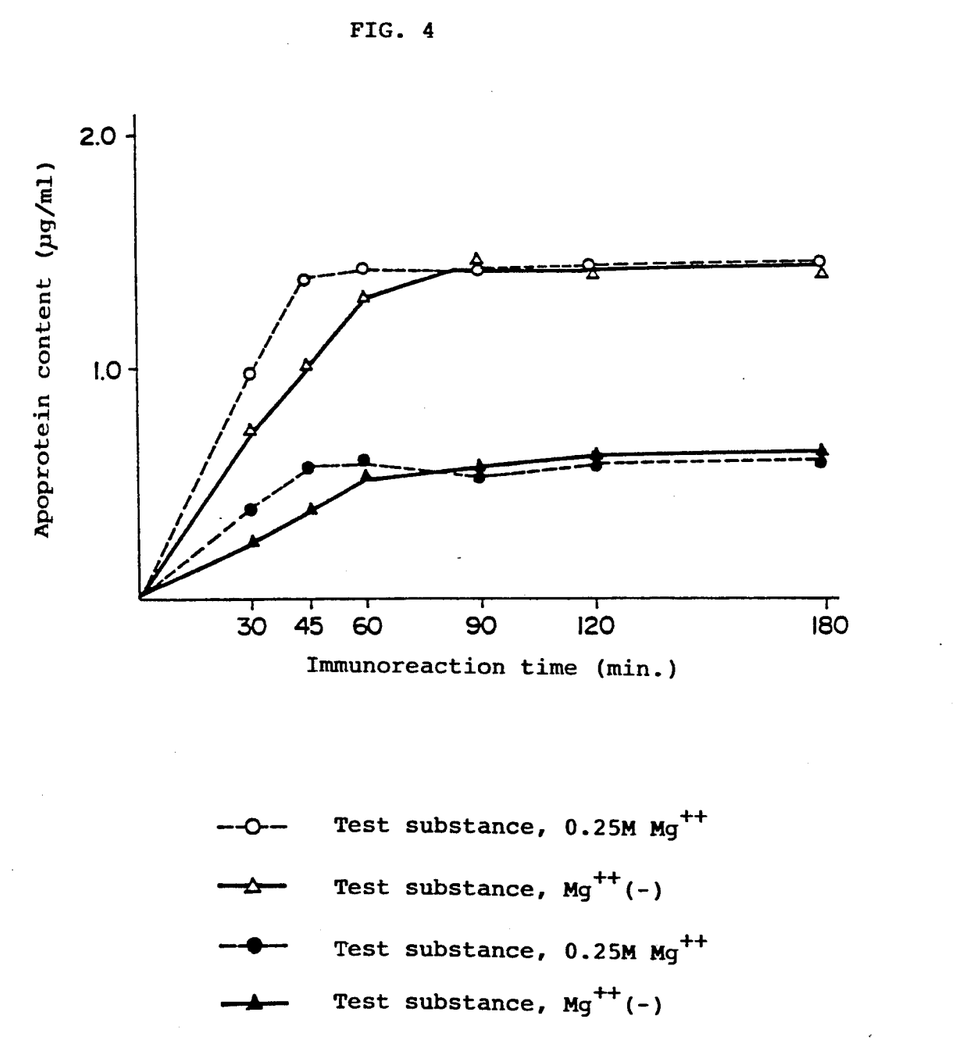
FIG. 4 shows the immunoreaction time versus lipoprotein concentration, i.e. measured values of the pulmonary surfactant (lipoprotein) in the amniotic fluid. The immunoassay was conducted in the presence and absence of 0.25M $Mg^{++}$.

It is apparent from FIG. 4 that the addition of $Mg^{++}$ is effective since the enzyme reaction is much accelerated by the presence of $Mg^{++}$ in the buffer.

INDUSTRIAL APPLICATIONS

The method proposed by the present invention makes it possible to quantitate the pulmonary surfactant apoproteins within the range of 10 to 640 μg/ml, with the variation coefficient kept below 6%. Human amniotic fluid can be subjected to quantitation if its quantity is 0.2 ml at the least.

According to the method of this invention, the determination of the pulmonary surfactant apoproteins in the test substance can be performed simply and conveniently in a short time, thus providing a useful method of determination and a kit to be used for such determination in case of an urgent disease such as IRDS, etc.

STATEMENT OF DEPOSIT

Hybridoma PC-6, which produces monoclonal antibody PC-6, and hybridoma PE-10, which produces monoclonal antibody PE-10, were deposited on Aug. 28, 1991 at the Fermentation Research Institute Agency of Industrial Science and Technology, 1-3, Higashi 1-chome Tsukuba-shi Ibaraki-ken, 305, Japan under the terms of the Budapest Treaty on the International Recognition of the Deposit of Microorganisms for the Purpose of Patent Procedure and have Deposition Numbers BP-3539 and BP-3540, respectively.

We claim:

1. A method of quantitation of human pulmonary surfactant in a test sample comprising reacting said sample with first and second monoclonal antibodies to form an immune complex thereof, wherein both antibodies bind specifically to a human pulmonary surfactant apoprotein as an antigen but each of which binds to a different epitope of said apoprotein, said first and second monoclonal antibodies are PC6 and PE10, respectively, or PE10 and PC6, respectively; and wherein said monoclonal antibody PC6 is produced by hybridoma PC6 which has FERM deposit number BP-3539 and said monoclonal antibody PE10 is produced by hybridoma PE10 which has FERM deposit number BP-3540; and determining the quantity of human pulmonary surfactant in said test sample by measuring the amount of said immune complex thus formed;

2. The method of quantitation of human pulmonary surfactant according to claim 1, wherein said method is characterized in that the first monoclonal antibodies are fixed to carriers and the second monoclonal antibodies are labeled.

3. The method of quantitation of human pulmonary surfactant according to claim 1 or claim 2, wherein the second monoclonal antibodies are biotinylated antibodies.

4. The method of quantitation of human pulmonary surfactant according to claim 1 or claim 2, wherein said reacting is performed at a temperature ranging from 40° C. to 50° C.

5. The method of quantitation of human pulmonary surfactant according to claim 1 or claim 2, further comprising performing said method in the presence of magnesium ions.

6. The method of quantitation of human pulmonary surfactant according to claim 2, further comprising adding skim milk as a blocking agent.

7. A reagent kit for determining human pulmonary surfactant in a test substance in an immunoreaction system said kit comprising: (1) first monoclonal antibodies fixed to a carrier, and (2) labeled second monoclonal antibodies, wherein both of said first and second monoclonal antibodies bind specifically to a human pulmonary surfactant apoprotein as an antigen, but each of said first and second monoclonal antibodies binds to a different epitope of said apoprotein; wherein said first and second monoclonal antibodies are PC6 and PE10, respectively, or PE10 and PC6, respectively; and wherein said monoclonal antibody PC6 is produced by hybridoma PC6 which has FERM deposit number BP-3539 and said monoclonal antibody PE10 is produced by hybridoma PE10 which has FERM deposit number BP-3540.

8. The reagent kit according to claim 7, wherein said labeled second monoclonal antibodies are is a biotinylated antibodies.

9. The reagent kit according to claim 8, further comprising enzyme-labeled avidin for detecting said labeled second antibodies.

* * * * *